United States Patent
Jackson et al.

(10) Patent No.: US 7,309,349 B2
(45) Date of Patent: Dec. 18, 2007

(54) FRICTION REDUCING LUBRICANT FOR STENT LOADING AND STENT DELIVERY SYSTEMS

(75) Inventors: Karen Paulette Jackson, Opa-Locka, FL (US); Christopher William Widenhouse, Pembroke Pines, FL (US)

(73) Assignee: Cordis Corporation, Miami Lakes, FL (US)

( * ) Notice: Subject to any disclaimer, the term of this patent is extended or adjusted under 35 U.S.C. 154(b) by 334 days.

(21) Appl. No.: 10/350,397

(22) Filed: Jan. 23, 2003

(65) Prior Publication Data

US 2004/0148007 A1    Jul. 29, 2004

(51) Int. Cl.
A61F 2/06    (2006.01)

(52) U.S. Cl. .................................... 623/1.11

(58) Field of Classification Search ............. 623/1.12, 623/1.11, 1.42–1.46
See application file for complete search history.

(56) References Cited

U.S. PATENT DOCUMENTS

| | | | |
|---|---|---|---|
| 4,665,771 A * | 5/1987 | Mitchell | 475/165 |
| 4,665,905 A * | 5/1987 | Brown | 602/16 |
| 4,732,152 A * | 3/1988 | Wallsten et al. | 623/1.11 |
| 4,733,665 A * | 3/1988 | Palmaz | 606/108 |
| 4,925,445 A * | 5/1990 | Sakamoto et al. | 604/528 |
| 5,519,042 A * | 5/1996 | Morris et al. | 514/378 |
| 5,800,517 A * | 9/1998 | Anderson et al. | 623/1.11 |
| 6,068,635 A * | 5/2000 | Gianotti | 606/108 |
| 6,090,035 A * | 7/2000 | Campbell et al. | 600/7 |
| 6,132,458 A | 10/2000 | Staehle et al. | |
| 6,149,680 A * | 11/2000 | Shelso et al. | 623/1.11 |
| 6,245,100 B1 * | 6/2001 | Davila et al. | 623/1.13 |
| 6,569,441 B2 * | 5/2003 | Kunz et al. | 424/423 |
| 6,640,412 B2 * | 11/2003 | Iancea | 29/505 |
| 6,673,385 B1 * | 1/2004 | Ding et al. | 427/2.28 |
| 7,052,512 B2 * | 5/2006 | Yang et al. | 623/1.46 |
| 2003/0225445 A1 * | 12/2003 | Derus et al. | 623/1.11 |

FOREIGN PATENT DOCUMENTS

EP    0 916 318 A    5/1999

* cited by examiner

Primary Examiner—(Jackie) Tan-Uyen Ho
Assistant Examiner—Melanie Tyson
(74) Attorney, Agent, or Firm—Carl J. Evens

(57) ABSTRACT

A system for loading self-expanding stents into a stent delivery system that comprises a lubricious coating on one or more components to substantially reduce the frictional forces associated with loading stents. The stents may be bare or coated stents. The lubricious coating comprises glycerol.

8 Claims, 7 Drawing Sheets

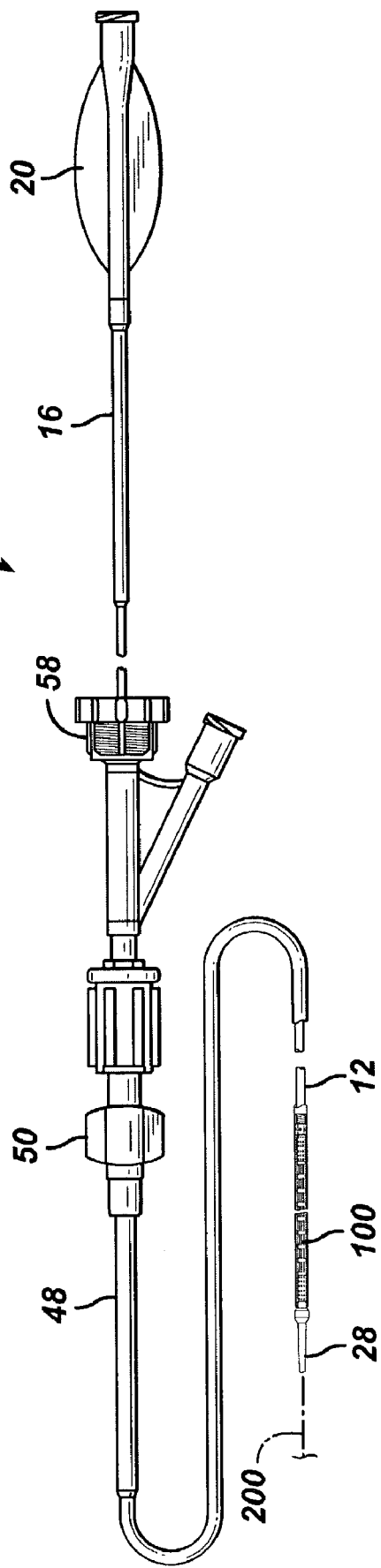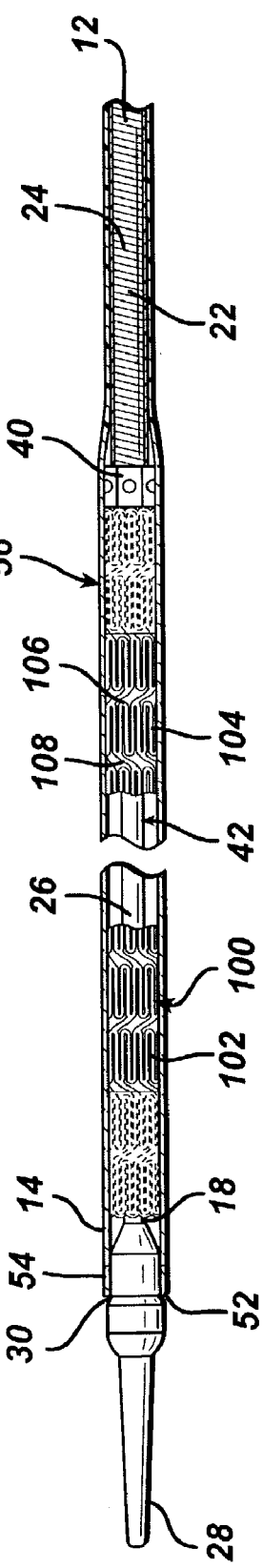
FIG. 1
FIG. 2

FRICTION REDUCING LUBRICANT FOR STENT LOADING AND STENT DELIVERY SYSTEMS

FIELD OF THE INVENTION

The present invention relates to stents for use within a body passageway or duct, which are particularly useful for repairing blood vessels narrowed or occluded by disease, and more particularly, to systems for delivering such stents.

BACKGROUND OF THE INVENTION

Various endoprosthesis assemblies, which include expandable stents, have been proposed or developed for use in association with angioplasty treatments and other medical procedures. The endoprosthesis assembly is generally percutaneously routed to a treatment site and the stent is expanded to maintain or restore the patency of a body passageway such as a blood vessel or bile duct. A stent is typically cylindrical in shape comprising an expandable open frame. The stent will typically expand either by itself (self-expanding stents) or will expand upon exertion of an outwardly directed radial force on an inner surface of the stent frame by a balloon catheter or the like.

Stents for endovascular implantation into a blood vessel or the like, to maintain or restore the patency of the passageway, have been deployed percutaneously to minimize the invasiveness associated with surgical exposure of the treatment site during coronary artery bypass. Percutaneous deployment is initiated by an incision into the vascular system of the patient, typically into the femoral artery. A tubular or sheath portion of an introducer is inserted through the incision and extends into the artery. The introducer has a central lumen which provides a passageway through the patient's skin and artery wall into the interior of the artery. An outwardly tapered hub portion of the introducer remains outside the patient's body to prevent blood from leaking out of the artery along the outside of the sheath. The introducer lumen includes a valve to block blood flow out of the artery through the introducer passageway. A distal end of a guide wire is passed through the introducer passageway into the patient's vasculature. The guide wire is threaded through the vasculature until the inserted distal end extends just beyond the treatment site. The proximal end of the guide wire extends outside the introducer.

For endovascular deployment, a stent, in an unexpanded or constricted configuration, is crimped onto a deflated balloon portion of a balloon catheter. The balloon portion is normally disposed near a distal end of the balloon catheter. The catheter has a central lumen extending its entire length. The distal end of the balloon catheter is threaded onto the proximal end of the guide wire. The distal end of the catheter is inserted into the introducer lumen and the catheter is pushed along the guide wire until the stent reaches the treatment site. At the treatment site, the balloon is inflated causing the stent to radially expand and assume an expanded configuration. When the stent is used to reinforce a portion of the blood vessel wall, the stent is expanded such that its outer diameter is approximately ten percent to twenty percent larger than the inner diameter of the blood vessel at the treatment site, effectively causing an interference fit between the stent and the blood vessel that inhibits migration of the stent. The balloon is deflated and the balloon catheter is withdrawn from the patient's body. The guide wire is similarly removed. Finally, the introducer is removed from the artery.

An example of a commonly used stent is given in U.S. Pat. No. 4,733,665 filed by Palmaz on Nov. 7, 1985. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second or expanded diameter. The expanded diameter is achieved through the application, by the balloon catheter positioned in the interior of the tubular shaped member, of a radially outwardly directed force.

However, such "balloon expandable" stents are often impractical for use in some vessels such as superficial arteries, like the carotid artery. The carotid artery is easily accessible from the exterior of the human body. A patient having a balloon expandable stent made from stainless steel or the like, placed in their carotid artery might be susceptible to sever injury through day to day activity. A sufficient force placed on the patient's neck, such as by falling, could cause the stent to collapse, resulting in injury to the patient. In order to prevent this, self-expanding stents have been proposed for use in such vessels. Self-expanding stents act similarly to springs and will recover to their expanded or implanted configuration after being crushed.

One type of self-expanding stent is disclosed in U.S. Pat. No. 4,665,771. The disclosed stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprises an outer catheter for holding the stent at its distal end, and an inner piston which pushes the stent forward once it is in position.

Other types of self-expanding stents use alloys such as Nitinol (Ni—Ti alloy), which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal, such as Nitinol, exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress is necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 to Jervis and U.S. Pat. No. 4,925,445 to Sakamoto et al.

Designing delivery systems for delivering self-expanding stents has proven difficult. One example of a prior art self-expanding stent delivery system is shown in U.S. Pat. No. 4,580,568 to Gianturco. This patent discloses a delivery apparatus which uses a hollow sheath, like a catheter. The sheath is inserted into a body vessel and navigated therethrough so that its distal end is adjacent the target site. The stent is then compressed to a smaller diameter and loaded into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remains stationary, thereby exposing the stent and allowing it to expand within the vessel.

However, delivering the stent through the entire length of the catheter may cause many problems, including possible damage to a vessel or the stent during its travel. In addition, it is often difficult to design a pusher having enough flexibility to navigate through the catheter, but also enough stiffness to push the stent out of the catheter. Therefore, it was determined that pre-loading the stent into the distal end of the catheter, and then delivering the catheter through the vessel to the target site may be a better approach. In order to ensure proper placement of the stent within catheter, it is often preferred that the stent be pre-loaded at the manufacturing site. Except this in itself has posed some problems. Because the catheter exerts a significant force on the self-expanding stent, which keeps it from expanding, the stent may tend to become imbedded within the wall of the catheter. When this happens, the catheter has difficulty sliding over the stent during delivery. This situation can result in the stent becoming stuck inside the catheter, or could damage the stent during delivery.

Another example of a prior art self-expanding stent delivery system is given in U.S. Pat. No. 4,732,152 to Wallsten et al. This patent discloses a probe or catheter having a self-expanding stent pre-loaded into its distal end. The stent is first placed within a flexible hose and compressed before it is loaded into the catheter. When the stent is at the delivery site the catheter and hose are withdrawn over the stent so that it can expand within the vessel. However, withdrawing the flexible hose over the stent during expansion could also cause damage to the stent.

Another problem associated with self-expanding stent delivery systems is the loading of the stent into the delivery system. The process of crimping the stent from its expanded state to a diameter suitable for transferring the stent to the stent delivery system can involve a number of steps and potentially high frictional forces. If a polymer and/or therapeutic agent coating is applied to the stent, the frictional forces required in loading the stent may be further increased. In certain circumstances, these forces may exceed the strength of the material being used for the loading process, including the strength of the stent or the stent delivery system, resulting in broken and unusable devices. In addition, the forces may exceed the strength of the adhesive bond between the polymeric and/or therapeutic agent coating and the stent, resulting in damage to the coating and/or the stent.

Accordingly, there is a need for a self-expanding stent delivery system which is able to navigate tortuous passageways, which prevents the stent from becoming embedded therein, which allows the physician to more easily and accurately deploy the stent within the target area. There is also a need to reduce the forces associated with loading a stent into a stent delivery system in order to prevent damage to the stent or any coatings thereon.

SUMMARY OF THE INVENTION

The present invention overcomes the potential disadvantages associated with self-expanding stent deployment systems as briefly described above.

In accordance with one aspect, the present invention is directed to a method for loading self-expanding stents into a stent delivery system. The method comprises reducing the diameter of the self-expanding stent to a diameter less than or equal to the inside diameter of an outer sheath of a catheter of the stent delivery system utilizing a compressive force member, transferring the reduced diameter self-expanding stent from the compressive force member into the stent delivery system utilizing a transfer tube, and applying a biocompatible lubricating material to at least one of the self-expanding stent, the compressive force member, the transfer tube member and the catheter to substantially reduce frictional forces.

In accordance with another aspect, the present invention is directed to a system for loading a self-expanding stent into a self-expanding stent delivery system. The system comprises a compressive force member for reducing the diameter of the self-expanding stent to a diameter less than or equal to the inside diameter of an outer sheath of a catheter of the stent delivery system, a transfer tube adapted to receive the reduced diameter stent from the compressive force member and load it into the catheter of the self-expanding stent delivery system, and a lubricating material affixed to at least one of the self-expanding stent, the compressive force member, the transfer tube and the catheter.

The loading of a self-expanding stent into a stent delivery system places high frictional forces on the stent. These frictional forces may cause damage to the stent and/or the stent delivery system. In addition, the coating of the stents with polymers and/or therapeutic agents may increase the forces inherent in loading. Therefore, in addition to potential damage to the stent, the coating may be removed. Accordingly, in order to reduce the frictional forces a biocompatible lubricant may be applied to the various loading devices as well as to the stent and to the catheter. The lubricant comprises glycerol.

BRIEF DESCRIPTION OF DRAWINGS

The foregoing and other features and advantages of the invention will be apparent from the following, more particular description of preferred embodiments of the invention, as illustrated in the accompanying drawings.

FIG. 1 is a simplified elevational view of a stent delivery apparatus made in accordance with the present invention.

FIG. 2 is a view similar to that of FIG. 1 but showing an enlarged view of the distal end of the apparatus having a section cut away to show the stent loaded therein.

DETAILED DESCRIPTION OF THE INVENTION

Figure 3:
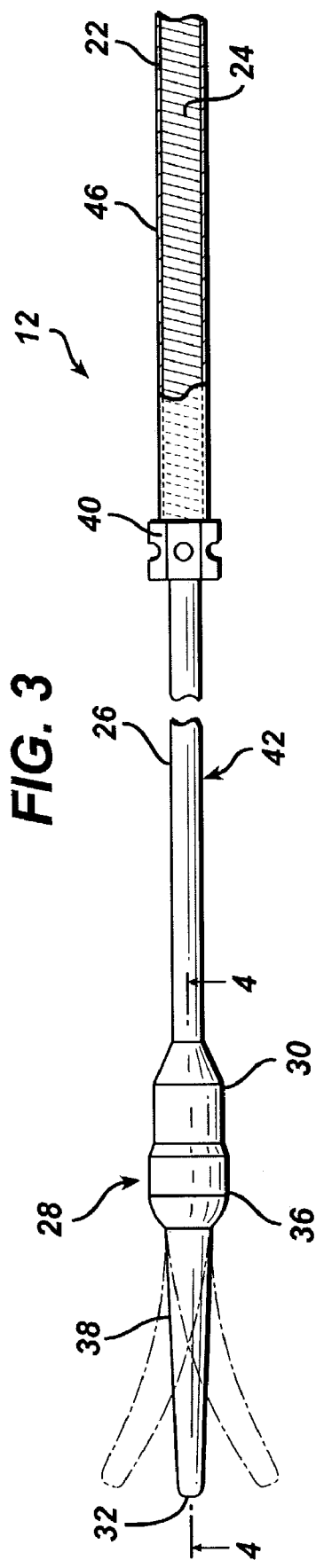
FIG. 3 is a simplified elevational view of the distal end of the inner shaft made in accordance with the present invention.
Figure 4:
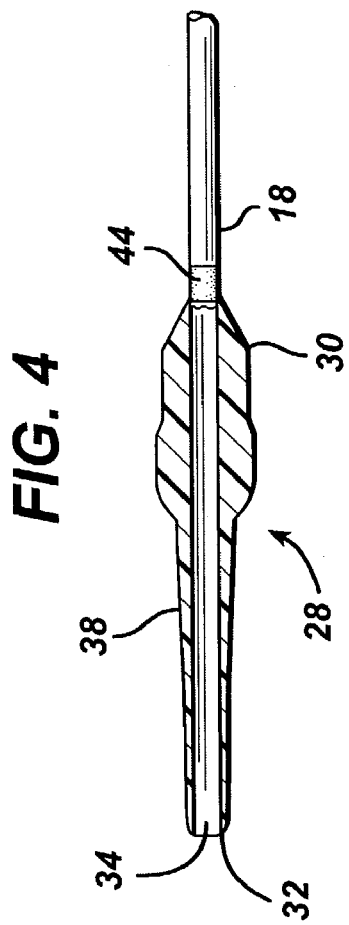
FIG. 4 is a cross-sectional view of FIG. 3 taken along lines 4-4.

FIGS. 1 and 2 illustrate an exemplary self-expanding stent delivery apparatus 10 in accordance with the present invention. Apparatus 10 comprises inner and outer coaxial tubes. The inner tube is called the shaft 12 and the outer tube is called the sheath 14. A self-expanding stent 100 is located within the sheath 14, wherein the stent 100 makes frictional contact with the sheath 14 and the shaft 12 is disposed coaxially within a lumen of the stent 100.

Shaft 12 has proximal and distal ends 16 and 18 respectively. The proximal end 16 of the shaft 12 has a Luer guidewire hub 20 attached thereto. As seen best from FIG. 10, the proximal end 16 of the shaft 12 is preferably a ground stainless steel hypotube. In one exemplary embodiment, the hypotube is stainless steel and has a 0.042 inch outside diameter at its proximal end and then tapers to a 0.036 inch outside diameter at its distal end. The inside diameter of the hypotube is 0.032 inch throughout its length. The tapered outside diameter is utilized to gradually change the stiffness of the hypotube along its length. This change in the hypotube stiffness allows for a more rigid proximal end or handle end that is needed during stent deployment. If the proximal end is not stiff enough, the hypotube section extending beyond the Tuohy Borst valve described below could buckle as the deployment forces are transmitted. The distal end of the hypotube is more flexible allowing for better track-ability in tortuous vessels. The distal end of the hypotube also needs to be flexible to minimize the transition between the hypotube and the coil section described below.

As will be described in greater detail below, shaft 12 has a body portion 22, wherein at least a section thereof is made from a flexible coiled member 24, looking very much like a compressed or closed coil spring. Shaft 12 also includes a distal portion 26, distal to body portion 22, which is preferably made from a coextrusion of high-density polyethylene and Nylon®. The two portions 22 and 26 are joined together by any number of means known to those of ordinary skill in the art including heat fusing, adhesive bonding, chemical bonding or mechanical attachment.

As best seen from FIG. 3, the distal portion 26 of the shaft 12 has a distal tip 28 attached thereto. Distal tip 28 may be made from any number of suitable materials known in the art including polyamide, polyurethane, polytetrafluoroethylene, and polyethylene including multi-layer or single layer construction. The distal tip 28 has a proximal end 30 whose diameter is substantially the same as the outer diameter of the sheath 14 which is immediately adjacent thereto. The distal tip 28 tapers to a smaller diameter from its proximal end 30 to its distal end 32, wherein the distal end 32 of the distal tip 28 has a diameter smaller than the inner diameter of the sheath 14.

The stent delivery apparatus 10 glides over a guide wire 200 (shown in FIG. 1) during navigation to the stent deployment site. As used herein, guidewire may also refer to similar guiding devices which have a distal protection apparatus incorporated herein. One preferred distal protection device is disclosed in published PCT Application 98/33443, having an international filing date of Feb. 3, 1998. As discussed above, if the distal tip 28 is too stiff it will overpower the guide wire path and push the guide wire 200 against the lumen wall and in some very tortuous settings the stent delivery apparatus 10 could prolapse the wire. Overpowering of the wire and pushing of the apparatus against the lumen wall can prevent the device from reaching the target area because the guide wire will no longer be directing the device. Also, as the apparatus is advanced and pushed against the lumen wall, debris from the lesion can be dislodged and travel upstream causing complications to distal vessel lumens. The distal tip 28 is designed with an extremely flexible leading edge and a gradual transition to a less flexible portion. The distal tip 28 may be hollow and may be made of any number of suitable materials, including 40D Nylon®. Its flexibility may be changed by gradually increasing the thickness of its cross-sectional diameter, whereby the diameter is thinnest at its distal end, and is thickest at its proximal end. That is, the cross-sectional diameter and wall thickness of the distal tip 28 increases as you move in the proximal direction. This gives the distal end 32 of the distal tip 28 the ability to be directed by the guidewire prior to the larger diameter and thicker wall thickness, less flexible portion, of the distal tip 28 overpowering the guidewire. Over-powering the wire, as stated above, is when the apparatus, due to its stiffness, dictates the direction of the device instead of following the wire.

The guidewire lumen 34 has a diameter that is matched to hug the recommended size guide wire so that there is a slight frictional engagement between the guidewire 200 and the guidewire lumen 34 of distal tip 28. The distal tip 28 has a rounded section 36 between its distal portion 32 and its proximal portion 30. This helps prevent the sheath 14 from slipping distally over the distal tip 28, and thereby exposing the squared edges of the sheath 14 to the vessel, which could cause damage thereto. This improves the device's "pushability." As the distal tip 28 encounters resistance it does not allow the sheath 14 to ride over it thereby exposing the sheath's 14 square cut edge. Instead the sheath 14 contacts the rounded section 36 of the distal tip 28 and thus transmits the forces applied to the distal tip 28. The distal tip 28 also has a proximally tapered section 38 which helps guide the distal tip 28 through the deployed stent 100 without providing a sharp edge that could grab or hang up on a stent strut end or other irregularity in the lumen inner diameter.

Attached to distal portion 26 of shaft 12 is a stop 40, which is proximal to the distal tip 28 and stent 100. Stop 40 may be made from any number of suitable materials known in the art, including stainless steel, and is even more preferably made from a highly radio-opaque material such as platinum, gold tantalum, or radio-opaque filled polymer. The stop 40 may be attached to shaft 12 by any suitable means, including mechanical or adhesive bonding, or by any other means known to those skilled in the art. Preferably, the diameter of stop 40 is large enough to make sufficient contact with the loaded stent 100 without making frictional contact with the sheath 14. As will be explained subsequently, the stop 40 helps to "push" the stent 100 or maintain its relative position during deployment, by preventing the stent 100 from migrating proximally within the sheath 14 during retraction of the sheath 14 for stent deployment. The radio-opaque stop 40 also aides in positioning the stent 100 within the target lesion area during deployment within a vessel, as is described below.

A stent bed 42 is defined as being that portion of the shaft 12 between the distal tip 28 and the stop 40 (FIG. 2). The stent bed 42 and the stent 100 are coaxial so that the distal portion 26 of the shaft 12 comprising the stent bed 42 is located within the lumen of stent 100. The stent bed 42 makes minimal contact with the stent 100 because of the space which exists between the shaft 12 and the sheath 14. As the stent 100 is subjected to temperatures at the austenite phase transformation it attempts to recover to its programmed shape by moving outwardly in a radial direction within the sheath 14. The sheath 14 constrains the stent 100 as will be explained in detail subsequently. Distal to the distal end of the loaded stent 100 attached to the shaft 12 is a radio-opaque marker 44 which may be made of platinum, iridium coated platinum, gold tantalum, stainless steel, radio-opaque filled polymer or any other suitable material known in the art.

Figure 10:
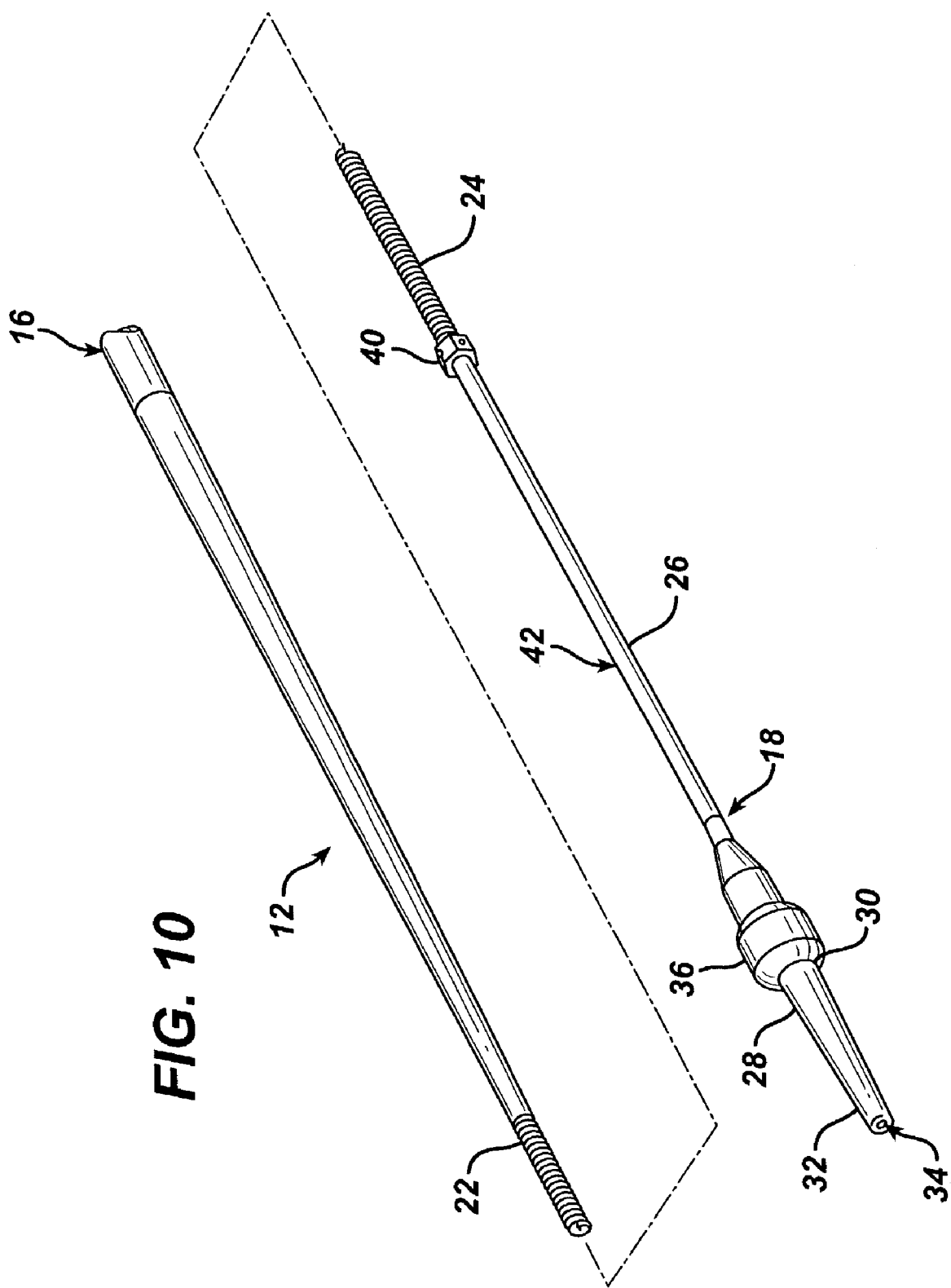
FIG. 10 is a simplified elevational view of a shaft for a stent delivery apparatus made in accordance with the present invention.

As seen from FIGS. 2, 3 and 10, the body portion 22 of the shaft 12 is made from a flexible coiled member 24, similar to a closed coil or compressed spring. During deployment of the stent 100, the transmission of compressive forces from the stop 40 to the Luer guidewire hub 20 is an important factor in deployment accuracy. A more compressive shaft 12 results in a less accurate deployment because the compression of the shaft 12 is not taken into account when visualizing the stent 100 under fluoroscopic imaging. However, a less compressive shaft 12 usually means less flexibility, which would reduce the ability of the apparatus 10 to navigate through tortuous vessels. A coiled assembly allows both flexibility and resistance to compression. When the apparatus 10 is being navigated through the arteries, the shaft 12 is not in compression and therefore the coiled member 24 is free to bend with the delivery path. As one deploys the stent 100, tension is applied to the sheath 14 as the sheath 14 is retracted over the encapsulated stent 100. Because the stent 100 is self-expanding it is in contact with the sheath 14 and the forces are transferred along the stent 100 and to the stop 40 of the shaft 12. This results in the shaft 12 being under compressive forces. When this happens, the flexible coiled member 24, no gaps between the coil members, transfers the compressive force from one coil to the next.

The flexible coiled member 24 further includes a covering 46 that fits over the flexible coiled member 24 to help resist buckling of the coiled member 24 in both bending and compressive modes. The covering 46 is an extruded polymer tube and is preferably a soft material that can elongate slightly to accommodate bending of the flexible coiled member 24, but does not allow the coils to ride over each other. Covering 46 may be made from any number of suitable materials including coextrusions of Nylon® and high-density polyethylene, polyurethane, polyamide, polytetrafluoroethylene, etc. The extrusion is also attached to the stop 40. Flexible coiled member 24 may be made of any number of materials known in the art including stainless steel, Nitinol, and rigid polymers. In one exemplary embodiment, flexible coiled member 24 is made from a 0.003 inch thick by 0.010 inch wide stainless steel ribbon wire. The wire may be round, or more preferably flat to reduce the profile of the flexible coiled member 24.

Sheath 14 is preferably a polymeric catheter and has a proximal end 48 terminating at a sheath hub 50 (FIG. 1). Sheath 14 also has a distal end 52 which terminates at the proximal end 30 of distal tip 28 of the shaft 12, when the stent 100 is in an un-deployed position as shown in FIG. 2. The distal end 52 of sheath 14 includes a radio-opaque marker band 54 disposed along its outer surface (FIG. 1). As will be explained below, the stent 100 is fully deployed when the marker band 54 is proximal to radio-opaque stop 40, thus indicating to the physician that it is now safe to remove the delivery apparatus 10 from the body.

As detailed in FIG. 2, the distal end 52 of sheath 14 includes an enlarged section 56. Enlarged section 56 has larger inside and outside diameters than the inside and outside diameters of the sheath 14 proximal to enlarged section 56. Enlarged section 56 houses the pre-loaded stent 100, the stop 40 and the stent bed 42. The outer sheath 14 tapers proximally at the proximal end of enlarged section 56 to a smaller size diameter. This design is more fully set forth in co-pending U.S. application Ser. No. 09/243,750 filed on Feb. 3, 1999, which is hereby incorporated herein by reference. One particular advantage to the reduction in the size of the outer diameter of sheath 14 proximal to enlarged section 56 is in an increase in the clearance between the delivery apparatus 10 and the guiding catheter or sheath that the delivery apparatus 10 is placed through. Using fluoroscopy, the physician will view an image of the target site within the vessel, before and after deployment of the stent, by injecting a radio-opaque solution through the guiding catheter or sheath with the delivery apparatus 10 placed within the guiding catheter. Because the clearance between the sheath 14, and the guiding catheter is increased by tapering or reducing the outer diameter of the sheath 14 proximal to enlarged section 56, higher injection rates may be achieved, resulting in better images of the target site for the physician. The tapering of sheath 14 provides for higher injection rates of radio-opaque fluid, both before and after deployment of the stent.

Figure 11:
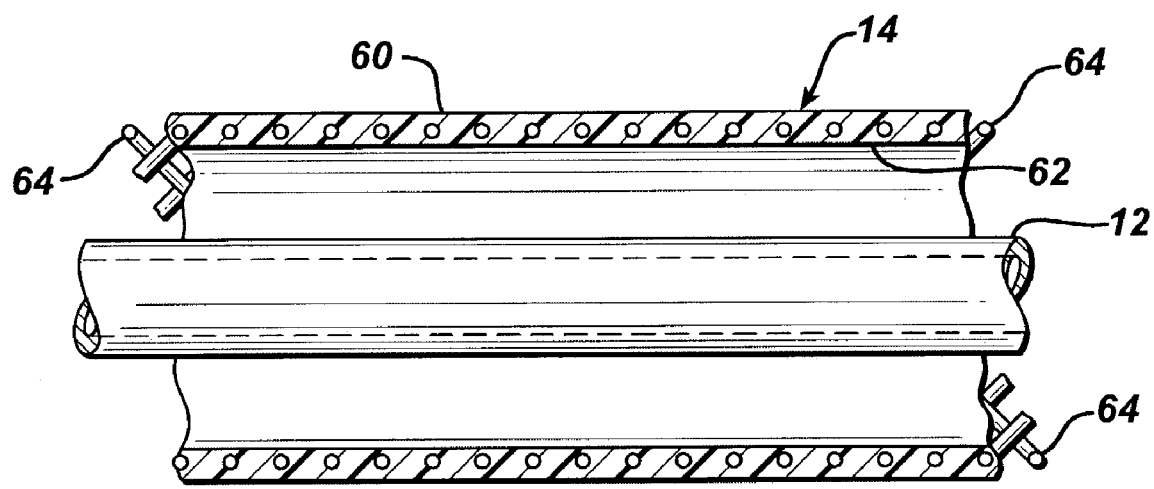
FIG. 11 is a partial cross-sectional view of the shaft and sheath of the stent delivery apparatus in accordance with the present invention.

A problem encountered with earlier self-expanding stent delivery systems is that of the stent becoming embedded within the sheath in which it is disposed. Referring to FIG. 11, there is illustrated a sheath construction which may be effectively utilized to substantially prevent the stent from becoming embedded in the sheath as well as provide other benefits as described in detail below. As illustrated, the sheath 14 comprises a composite structure of at least two layers and preferably three layers. The outer layer 60 may be formed from any suitable biocompatible material. Preferably, the outer layer 60 is formed from a lubricious material for ease of insertion and removal of the sheath 14. In a preferred embodiment, the outer layer 60 comprises a polymeric material such as Nylon®. The inner layer 62 may also be formed from any suitable biocompatible material. For example, the inner layer 62 may be formed from any number of polymers including polyethylene, polyamide or polytetrafluroethylene. In a preferred embodiment, the inner layer 62 comprises polytetrafluroethylene. Polytetrafluroethylene is also a lubricious material which makes stent delivery easier, thereby preventing damage to the stent 100. The inner layer 62 may also be coated with another material to increase the lubricity thereof for facilitating stent deployment. Any number of suitable biocompatible materials may be utilized. In an exemplary embodiment, silicone based coatings may be utilized. Essentially, a solution of the silicone-based coating may be injected through the apparatus and allowed to cure at room temperature. The amount of silicone-based coating utilized should be minimized to prevent transference of the coating to the stent 100. Sandwiched between the outer and inner layers 60 and 62, respectively, is a wire reinforcement layer 64. The wire reinforcement layer 64 may take on any number of configurations. In the exemplary embodiment, the wire reinforcement layer 64 comprises a simple under and over weave or braiding pattern. The wire used to form the wire reinforcement layer 64 may comprise any suitable material and any suitable cross-sectional shape. In the illustrated exemplary embodiment, the wire forming the wire reinforcement layer 64 comprises stainless steel and has a substantially circular cross-section. In order to function for its intended purpose, as described in detail below, the wire has a diameter of 0.002 inches.

The three layers 60, 62, and 64 comprising the sheath 14 collectively enhance stent deployment. The outer layer 60 facilitates insertion and removal of the entire apparatus 10. The inner layer 62 and the wire reinforcement layer 64 function to prevent the stent 100 from becoming embedded in the sheath 14. Self-expanding stents such as the stent 100 of the present invention tend to expand to their programmed diameter at a given temperature. As the stent attempts to undergo expansion, it exerts a radially outward directed force and may become embedded in the sheath 14 restraining it from expanding. Accordingly, the wire reinforcing layer 64 provides radial or hoop strength to the inner layer 62 thereby creating sufficient resistance to the outwardly directed radial force of the stent 100 within the sheath 14. The inner layer 62, also as discussed above, provides a lower coefficient of friction surface to reduce the forces required to deploy the stent 100 (typically in the range from about five to eight pounds). The wire reinforcement layer 64 also provides tensile strength to the sheath 14. In other words, the wire reinforcement layer 64 provides the sheath 14 with better pushability, i.e., the ability to transmit a force applied by the physician at a proximal location on the sheath 14 to the distal tip 28, which aids in navigation across tight stenotic lesions within the vasculature. Wire reinforcement layer 64 also provides the sheath 14 with better resistance to elongation and necking as a result of tensile loading during sheath retraction for stent deployment.

The sheath 14 may comprise all three layers along its entire length or only in certain sections, for example, along the length of the stent 100. In a preferred embodiment, the sheath 14 comprises all three layers along its entire length.

Prior art self-expanding stent delivery systems did not utilize wire reinforcement layers. Because the size of typical self-expanding stents is relatively large, as compared to balloon expandable coronary stents, the diameter or profile of the delivery devices therefor had to be large as well. However, it is always advantageous to have delivery systems which are as small as possible. This is desirable so that the devices can reach into smaller vessels and so that less trauma is caused to the patient. However, as stated above, the advantages of a thin reinforcing layer in a stent delivery apparatus outweighs the disadvantages of slightly increased profile.

Figure 12:
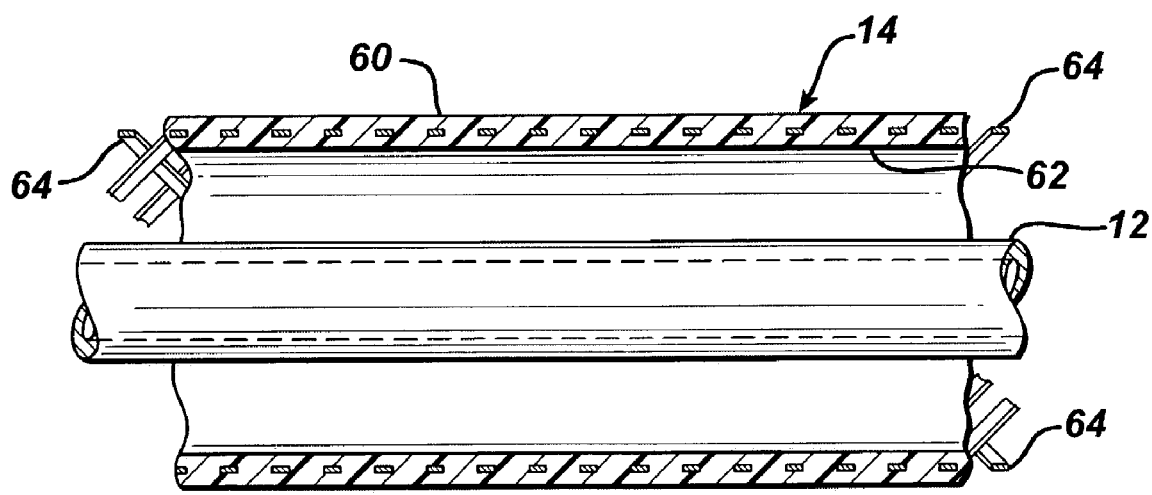
FIG. 12 is a partial cross-sectional view of the shaft and modified sheath of the stent delivery system in accordance with the present invention.

In order to minimize the impact of the wire reinforcement layer on the profile of the apparatus 10, the configuration of the wire reinforcement layer 64 may be modified. For example, this may be accomplished in a number of ways, including changing the pitch of the braid, changing the shape of the wire, changing the wire diameter and/or changing the number of wires utilized. In a preferred embodiment, the wire utilized to form the wire reinforcement layer comprises a substantially rectangular cross-section as illustrated in FIG. 12. In utilizing a substantially rectangular cross-section wire, the strength features of the reinforcement layer 64 may be maintained with a significant reduction in the profile of the delivery apparatus. In this preferred embodiment, the rectangular cross-section wire has a width of 0.003 inches and a height of 0.001 inches. Accordingly, braiding the wire in a similar manner to FIG. 11, results in a fifty percent decrease in the thickness of the wire reinforcement layer 64 while maintaining the same beneficial characteristics as the 0.002 round wire. The flat wire may comprise any suitable material, and preferably comprises stainless steel.

In another alternate exemplary embodiment, the sheath of the delivery system may comprise an inner layer or coating on its inner surface which substantially prevents the stent from becoming embedded therein while increasing the lubricity thereof. This inner layer or coating may be utilized with the sheaths illustrated in FIGS. 11 and 12 or as an alternative means to decrease the stent deployment forces. Given the thinness of the coating, as described in more detail below, the overall profile of the delivery system will be minimally impacted if at all. In addition to increasing the strength of the sheath and making it more lubricious, the coating is extremely biocompatible which is important since it does make contact with blood, albeit at least temporarily.

Essentially, in the exemplary embodiment, a hard and lubricious coating is applied to or affixed to the inner surface of the sheath of the self-expanding delivery system. The coating provides a number of advantages over currently utilized self-expanding stent delivery systems. For example, the coating provides a hard surface against which the stent exerts a radially outward directed force. As described above, self-expanding stents have a constant outward force of expansion when loaded into the delivery system. This constant and relatively high radially outward directed force can force the polymeric materials that comprise the sheath of the delivery system to creep and allow the stent to become embedded into the polymer surface. As stent platforms are developed with larger diameter stents and subsequently higher radially outward directed forces, the occurrence of this phenomenon will increase. Consequently, embedding increases the force required to deploy the stent because it causes mechanical resistance to the movement of the stent inside the delivery system, thereby preventing accurate deployment and causing potential damage to the stent. In addition, the coating is lubricious, i.e. it has a low coefficient of friction. A lubricious coating, as stated above, functions to further reduce the force required to deploy the stent, thereby increasing the facility by which the stents are delivered and deployed by physicians. This is especially important with respect to newer larger diameter stent designs and/or drug/polymer coated stent designs that have either increased radial forces, increased profile or increased overall diameter. A lubricious coating is particularly advantageous with respect to drug/polymer coated stents. Accordingly, the coating functions to prevent the stent from embedding in the sheath of the delivery system prior to deployment and reducing the friction between the sheath and the stent, both of which will reduce the deployment forces.

Various drugs, agents or compounds may be locally delivered via medical devices such as stents. For example, rapamycin and/or heparin may be delivered by a stent to reduce restenosis, inflammation and coagulation. Various techniques for immobilizing the drugs, agents or compounds onto the stent are known; however, maintaining the drugs, agents or compounds on the stent during delivery and positioning is critical to the success of the procedure or treatment. For example, removal of the drug, agent or compound during delivery of the stent can potentially cause failure of the device. For a self-expanding stent, the retraction of the restraining sheath may cause the drugs, agents or compounds to rub off the stent. Therefore, prevention of this potential problem is important to have successful therapeutic medical devices such as stents.

Figure 13:
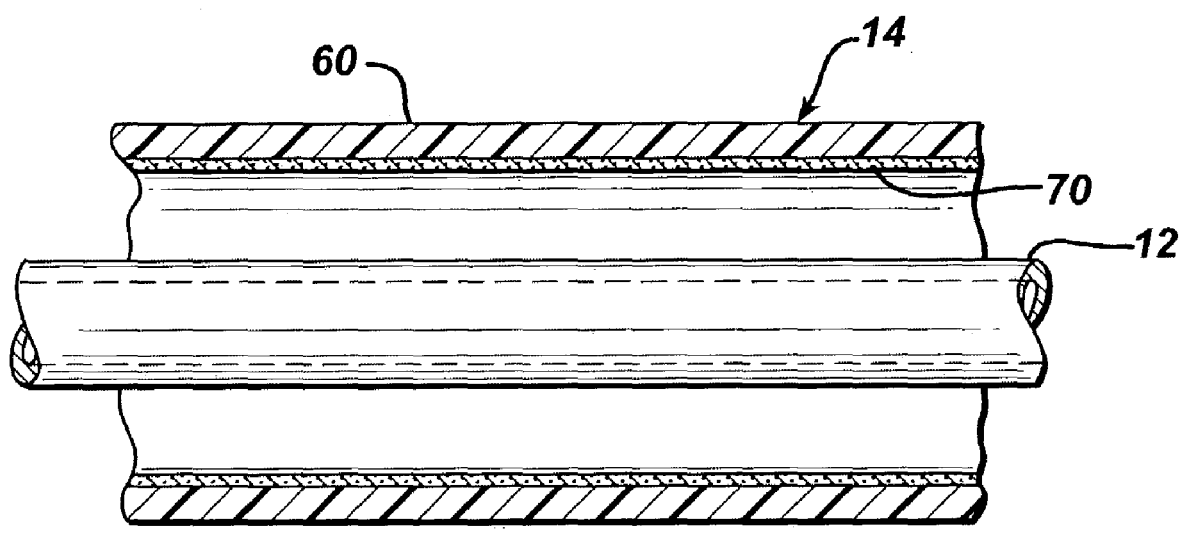
FIG. 13 is a partial cross-sectional view of the shaft and modified sheath of the stent delivery system in accordance with the present invention.

FIG. 13 illustrates a partial cross-sectional view of the shaft and modified sheath of the stent delivery system in accordance with an exemplary embodiment of the present invention. As shown, a coating or layer of material 70 is affixed or otherwise attached to the inner circumference of the sheath 14. As stated above, the coating or layer of material 70 comprises a hard and lubricious substance. In a preferred embodiment, the coating 70 comprises pyrolytic carbon. Pyrolytic carbon is a well-known substance that is utilized in a wide variety of implantable medical prostheses and is most commonly utilized in cardiac valves, as it combines high strength with excellent tissue and blood compatibility.

Pyrolytic carbon's usefulness in the implantable medical device area is a result of its unique combination of physical and chemical characteristics, including chemical inertness, isotrophy, low weight, compactness and elasticity. Pyrolytic carbon belongs to a specific family of turbostratic carbons which are similar to the structure of graphite. In graphite, the carbon atoms are covalently bonded in planar hexagonal arrays that are stacked in layers with relatively weak interlayer bonding. In turbostratic carbons, the stacking sequence is disordered and distortions may exist within each of the layers. These structural distortions in the layers are responsible for the superior ductility and durability of pyrolytic carbon. Essentially, the microstructure of pyrolytic carbon makes the material durable, strong and wear resistant. In addition, pyrolytic carbon is highly thromboresistant and has inherent cellular biocompatability with blood and soft tissue.

The pyrolytic carbon layer 70 may be deposited along the entire length of the sheath 14 or only in proximity to the stent bed 42, illustrated in FIGS. 2 and 3. In a preferred embodiment, the pyrolytic carbon layer 70 is affixed to the sheath 14 in the region of the stent bed 42. The pyrolytic carbon layer 70 may be deposited or affixed to the inner circumference utilizing any number of known techniques that are compatible or usable with the polymeric materials comprising the sheath 14. The thickness of the pyrolytic carbon layer 70 is selected such that it prevents or substantially reduces the possibility of the stent becoming embedded in the sheath 14 without decreasing the flexibility of the sheath 14 or increasing the profile of the self-expanding stent delivery system. As described above, it is important that the sheath be both flexible and pushable to navigate tortuous pathways within the body. In addition, it is always desirable to reduce the profile of percutaneously delivered devices.

As stated above, pyrolytic carbon surfaces are recognized as biocompatible, especially with respect to blood contact applications. This is, however, only a minor benefit in terms of stent delivery applications because the location of the pyrolytic carbon layer 70 within the sheath 14 is only minimally exposed to blood and is only within the body for a duration sufficient to deliver a stent.

The pyrolytic carbon layer 70 may be affixed to the lumen of the sheath in any number of ways as mentioned above. In one exemplary embodiment, the pyrolytic carbon layer 70 may be directly affixed to the lumen of the sheath 14. In another exemplary embodiment, the pyrolytic carbon layer 70 may be indirectly applied to the lumen of the sheath 14 by first applying it to a variety of substrates, also utilizing any number of known techniques. Regardless of whether the pyrolytic carbon layer 70 is deposited directly onto the sheath 14 or first onto a substrate, any number of known techniques may be utilized, for example, chemical vapor deposition. In chemical vapor deposition, the carbon material is deposited from gaseous hydrocarbon compounds on suitable underlying substrates, e.g. carbon materials, metals, ceramics as well as other materials, at temperatures ranging from about 1000K to about 2500K. At these temperatures, one can understand the need to possibly utilize substrates. Any suitable biocompatible, durable and flexible substrate may be utilized and then affixed to the lumen of the sheath 14 utilizing well-known techniques such as adhesives. As stated above, profile and flexibility are important design characteristics; accordingly, the type of substrate material chosen and/or its thickness should be considered. It is important to note that a wide range of microstructures, e.g. isotropic, lamellor, substrate-nucleated and a varied content of remaining hydrogen can occur in pyrolytic carbons, depending on the deposition conditions, including temperature, type, concentration and flow rates of the source gas and surface area of the underlying substrate.

Other techniques which may be utilized to affix the pyrolytic carbon layer 70 directly onto the sheath 14 or onto a substrate include pulsed laser ablation deposition, radio frequency plasma modification, physical vapor deposition as well as other known techniques. In addition to pyrolytic carbon, other materials that might be beneficial in providing similar properties include diamond-like carbon coatings, silane/silicon glass like surfaces and thin ceramic coatings such as alumina, hydroxyapatite and titania.

In an alternate exemplary embodiment, the pyrolytic carbon coating may be applied with a controlled finite porosity as briefly described above. This controlled finite porosity provides two distinct advantages. First, the porosity may serve to reduce the contact surface area if the stent with the pyrolytic carbon coating 70, thereby reducing the friction between the stent and the inner lumen of the sheath 14. Second, lubricious materials such as biocompatible oils, waxes and powders could be infused or impregnated within the porous surface of the coating thereby providing a reservoir of lubricious material further reducing the frictional coefficient.

FIGS. 1 and 2 show the stent 100 as being in its fully un-deployed position. This is the position the stent is in when the apparatus 10 is inserted into the vasculature and its distal end is navigated to a target site. Stent 100 is disposed around the stent bed 42 and at the distal end 52 of sheath 14. The distal tip 28 of the shaft 12 is distal to the distal end 52 of the sheath 14. The stent 100 is in a compressed state and makes frictional contact with the inner surface of the sheath 14.

When being inserted into a patient, sheath 14 and shaft 12 are locked together at their proximal ends by a Tuohy Borst valve 58. This prevents any sliding movement between the shaft 12 and sheath 14, which could result in a premature deployment or partial deployment of the stent 100. When the stent 100 reaches its target site and is ready for deployment, the Tuohy Borst valve 58 is opened so that the sheath 14 and shaft 12 are no longer locked together.

Figure 5:
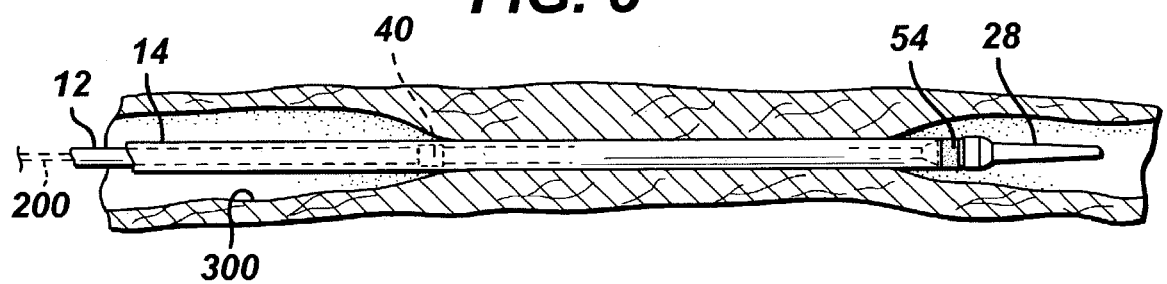
FIGS. 5 through 9 are partial cross-sectional views of the apparatus of the present invention sequentially showing the deployment of the self-expanding stent within the vasculature.
Figure 6:
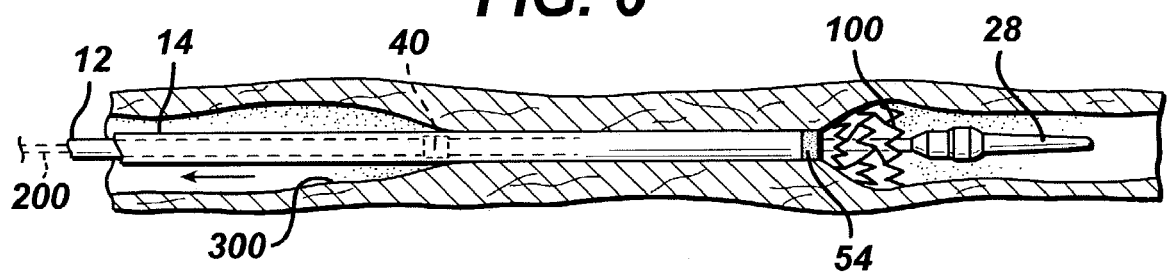
Figure 7:
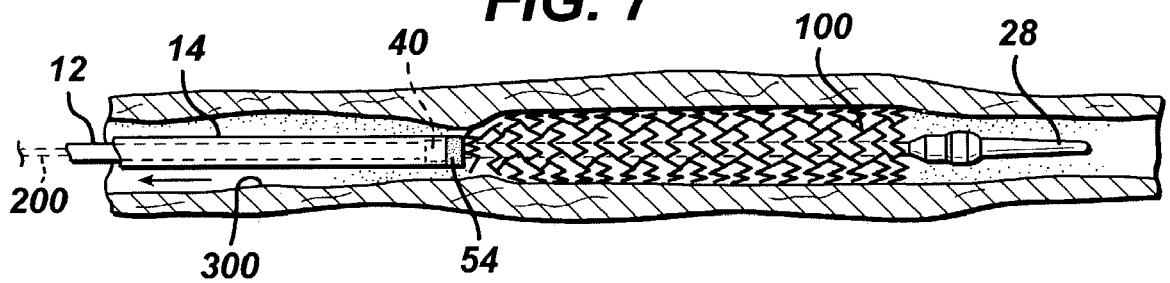
Figure 8:
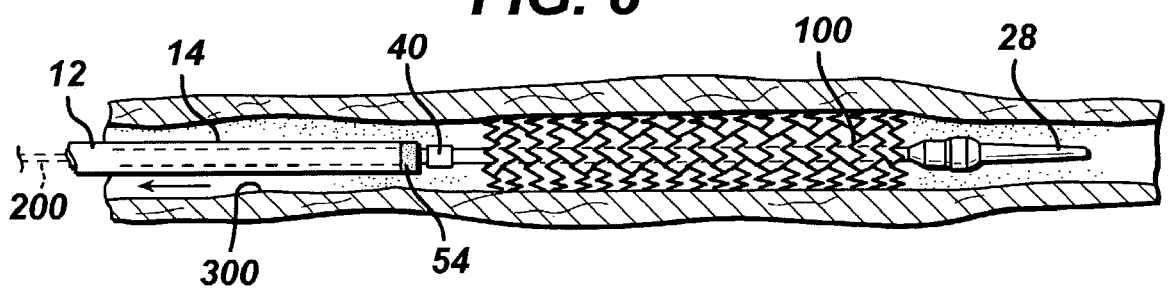

The method under which delivery apparatus 10 deploys stent 100 may best be described by referring to FIGS. 5-9. In FIG. 5, the delivery apparatus 10 has been inserted into a vessel 300 so that the stent bed 42 is at a target diseased site. Once the physician determines that the radio-opaque marker band 54 and stop 40 on shaft 12 indicating the ends of stent 100 are sufficiently placed about the target disease site, the physician would open Tuohy Borst valve 58. The physician would then grasp the Luer guidewire hub 20 of shaft 12 so as to hold shaft 12 in a fixed position. Thereafter, the physician would grasp the Tuohy Borst valve 58, attached proximally to sheath 14, and slide it proximal, relative to the shaft 12 as shown in FIGS. 6 and 7. Stop 40 prevents the stent 100 from sliding back with sheath 14, so that as the sheath 14 is moved back, the stent 100 is effectively "pushed" out of the distal end 52 of the sheath 14, or held in position relative to the target site. Stent 100 should be deployed in a distal to proximal direction to minimize the potential for creating emboli with the diseased vessel 300. Stent deployment is complete when the radio-opaque band 54 on the sheath 14 is proximal to radio-opaque stop 40, as shown in FIG. 8. The apparatus 10 can now be withdrawn through stent 100 and removed from the patient.

Figure 9:
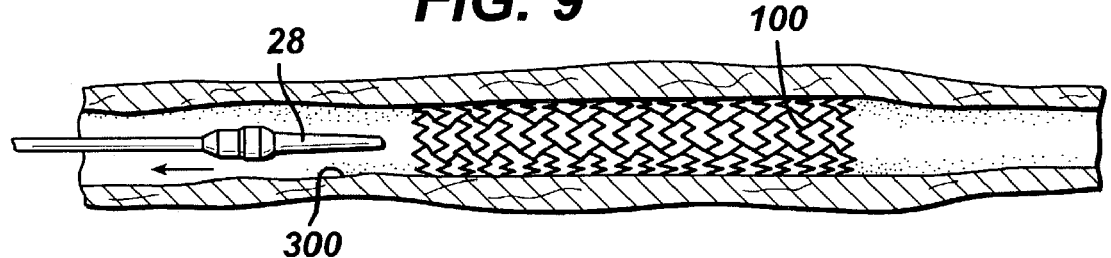

FIGS. 2 and 9 show a preferred embodiment of a stent 100, which may be used in conjunction with the present invention. Stent 100 is shown in its unexpanded compressed state, before it is deployed, in FIG. 2. Stent 100 is preferably made from a superelastic alloy such as Nitinol. Most preferably, the stent 100 is made from an alloy comprising from about 50.5 percent (as used herein these percentages refer to atomic percentages) Ni to about 60 percent Ni, and most preferably about 55 percent Ni, with the remainder of the alloy Ti. Preferably, the stent 100 is such that it is superelastic at body temperature, and preferably has an Af in the range from about twenty-one degrees C. to about thirty-seven degrees C. The superelastic design of the stent makes it crush recoverable which, as discussed above, can be used as a stent or frame for any number of vascular devices for different applications.

Stent 100 is a tubular member having front and back open ends a longitudinal axis extending there between. The tubular member has a first smaller diameter, FIG. 2, for insertion into a patient and navigation through the vessels, and a second larger diameter for deployment into the target area of a vessel. The tubular member is made from a plurality of adjacent hoops 102 extending between the front and back ends. The hoops 102 include a plurality of longitudinal struts 104 and a plurality of loops 106 connecting adjacent struts, wherein adjacent struts are connected at opposite ends so as to form a substantially S or Z shape pattern. Stent 100 further includes a plurality of curved bridges 108, which connect adjacent hoops 102. Bridges 108 connect adjacent struts together at bridge to loop connection points which are offset from the center of a loop.

The above described geometry helps to better distribute strain throughout the stent, prevents metal to metal contact when the stent is bent, and minimizes the opening size between the features, struts, loops and bridges. The number of and nature of the design of the struts, loops and bridges are important factors when determining the working properties and fatigue life properties of the stent. Preferably, each hoop has between twenty-four to thirty-six or more struts. Preferably the stent has a ratio of number of struts per hoop to strut length (in inches) which is greater than two hundred. The length of a strut is measured in its compressed state parallel to the longitudinal axis of the stent.

In trying to minimize the maximum strain experienced by features, the stent utilizes structural geometries which distribute strain to areas of the stent which are less susceptible to failure than others. For example, one vulnerable area of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge to loop connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and it's ability to trap embolic material.

Figure 14:
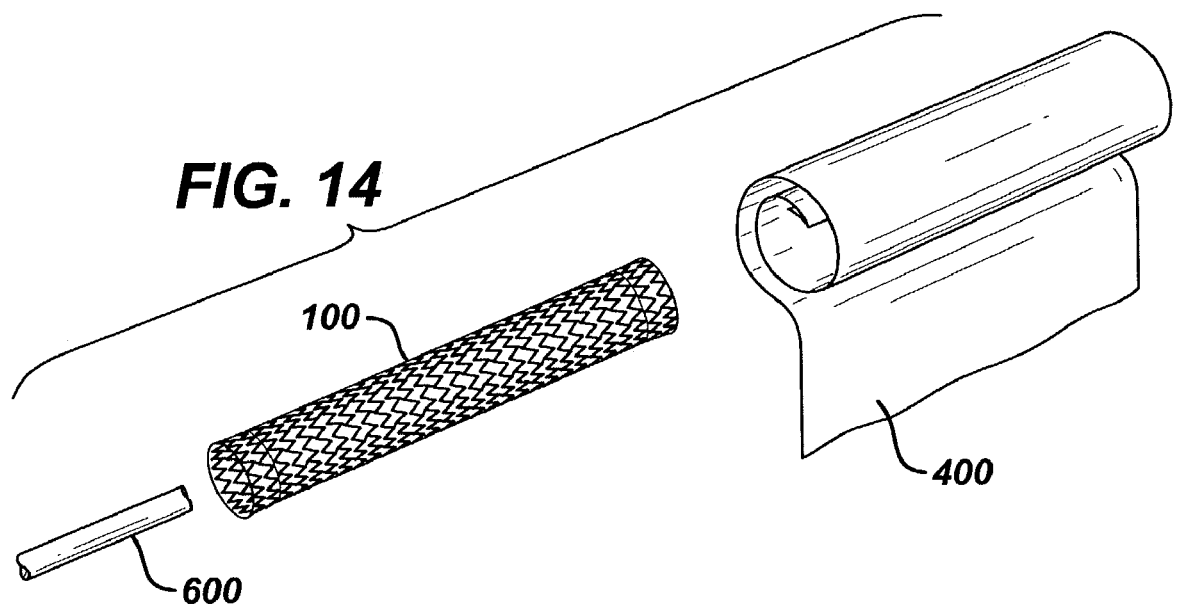
FIG. 14 is a first exploded perspective view of the loading process in accordance with the present invention.

In order that a self-expanding stent may be implanted into a patient, the stent must be loaded into a stent delivery system. In one exemplary procedure for transferring an expanded stent into the stent delivery system, a number of steps and tools are utilized. The first step in the procedure involves crimping the expanded stent to a smaller diameter. This first step may be accomplished in a number of ways. In the exemplary embodiment, the stent is wrapped in a film 400 and a restrictive or compressive force is imparted to the stent 100 to decrease its diameter as illustrated in FIG. 14.

Figure 15:
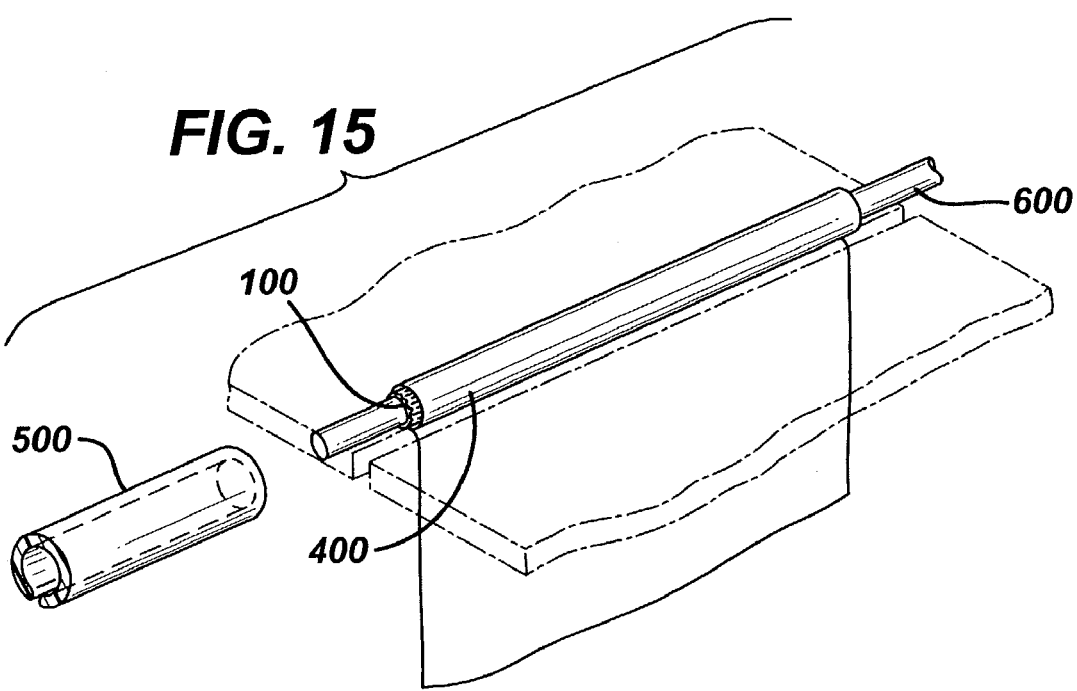
FIG. 15 is a second exploded perspective view of the loading process in accordance with the present invention.

The film 400 may comprise any suitable high strength material. In addition, as the film 400 is used to impart its restrictive forces, frictional forces develop between the film 400 and the stent 100. Accordingly, in addition to having a high strength material, the material should also preferably have a low coefficient of friction. In the exemplary embodiment, the film 400 comprises polytetrafluoroethylene. The next step in the procedure involves transferring the crimped stent 100 from the film wrap 400 into a transfer tube 500 as illustrated in FIG. 15. A mandrel 600 or any other suitable tool may be utilized to push the crimped stent 100 from the film wrap 400 into the transfer tube 500. In this step, the force applied to the stent 100 through the mandrel 600 or other tool is required to overcome the frictional forces of the film wrap 400 and of the transfer tube 500. The transfer tube 500 may be formed from any suitable material, including polytetrafluoroethylene. The final step in the procedure involves transferring the crimped stent 100 from the transfer tube 500 into the delivery catheter. The delivery catheter may comprise any suitable delivery device, including the delivery devices described herein. A mandrel 600 or other similar tool or device may be utilized to push the crimped stent from the transfer tube into the catheter.

The process of crimping the stent from the expanded state into a suitable diameter to be transferred into the stent delivery system involves a number of steps and high frictional forces as briefly described above. It is possible that these forces can exceed the strength of the materials being used for the loading process, including the strength of the stent or the stent delivery system, resulting in damaged and unusable devices.

In accordance with one exemplary embodiment, a lubricating agent may be utilized to substantially reduce the high frictional forces associated with stent crimping and loading. Any number of biocompatible lubricating agents may be utilized. In one exemplary embodiment, glycerol, also known as glycerin, glycerine or 1,2,3-Propanetriol, may be utilized as the lubricating agent to reduce the frictional forces associated with building a stent into a stent delivery system.

The glycerol may be applied directly to the stent or to the tools used to transfer the expanded stent into the stent delivery system. For example, the glycerol may be applied to the crimping film 400, to the transfer tube 500 and/or the catheter of the stent delivery system to provide for sufficient lubrication. The glycerol may be applied to any or all of the above described devices, as well as any combination thereof. The glycerol may be rinsed or removed from the catheter prior to packaging of the device if necessary. However, glycerol exists in the human body in finite concentrations as a byproduct of the metabolism of triglycerides into fatty acids and glycerol. Because there is a finite concentration of glycerol circulating in the blood system, any additional glycerol released into the body during stent placement will be metabolized in a manner consistent with the metabolism of naturally occurring glycerol.

The glycerol may be applied as a solution, for example, an aqueous solution. Other solvents may be utilized if they are determined to be compatible with the drugs, agents and/or compounds described below.

As described above, various drugs, agents and/or compounds may be locally delivered via medical devices. For example, rapamycin and heparin may be delivered by a stent to reduce restenosis, inflammation, and coagulation. Various techniques for immobilizing the drugs, agents and/or compounds onto the device are known in the art. For example, a drug like rapamycin may be incorporated into a polymeric matrix, such as polyvinylidinefluoride/hexafluoropropylene, and applied to the stent utilizing any number of known techniques. Maintaining the drugs, agents and/or compounds on the stent or other medical device is critical to the success of the procedure or treatment.

The use of polymer and/or a drug coating on a stent may increase the forces of building a stent into a stent delivery system. In the case of polymer coated stents, the loading forces may sometimes exceed the strength of the adhesive bond between the coating and the stent, resulting in damage to the coating and unusable stents. Accordingly, a lubricating agent, as described above, may be utilized to substantially reduce or minimize the frictional forces involved. It is important to note, however, that while any number of lubricious materials may be utilized, it is a basic requirement that the material be biocompatible, that the material not interfere with the actions/effectiveness of the drugs, agents and/or compounds, and that the material not interfere with the materials utilized to immobilize the drugs, agents and/or compounds on the stent. Glycerol is known as an acceptable excipient for formulations with rapamycin and will not degrade or otherwise affect polyvinylidenefluoride/hexafluoropropylene.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for loading self-expanding stents into a stent delivery system comprising:

positioning a self-expanding stent on a mandrel;

reducing the diameter of the self-expanding stent to a diameter less than or equal to the inside diameter of an outer sheath of a catheter of the stent delivery system utilizing a film wrap;

transferring the reduced diameter self-expanding stent from the film wrap into the stent delivery system utilizing a stand alone transfer tube, the transfer tube including a slotted cylinder for removing the film wrap; and applying a separate and distinct biocompatible lubricating material to at least one of the self-expanding stent, the film wrap, the transfer tube member and the catheter to substantially reduce frictional forces thereby reducing the loading forces.

2. The method for loading self-expanding stents with a stent delivery system according to claim 1, wherein the step of applying a separate and distinct biocompatible lubricating material comprises coating at least one of the self-expanding stent, the film wrap, the transfer tube member and the catheter with glycerol.

3. A system for loading a self-expanding stent into a self-expanding stent delivery system comprising:

a film wrap for reducing the diameter of the self expanding stent to a diameter less than or equal to the inside diameter of an outer sheath of a catheter of the stent delivery system:

a stand alone transfer tube adapted to receive the reduced diameter stent from the film wrap and load it into the catheter of the self-expanding stent delivery system, the transfer tube including a slotted cylinder for removing the film wrap therethrough; and a separate and distinct lubricating material affixed to at least one of the self-expanding stent, the compressive force member, the transfer tube and the catheter, the lubricating material reducing the loading forces.

4. The system for loading a self-expanding stent into a self-expanding stent delivery system according to claim 3, wherein the stent comprises a polymeric coating.

5. The system for loading a self-expanding stent into a self-expanding stent delivery system according to claim 3, wherein the stent comprises a therapeutic agent coating.

6. The system for loading a self-expanding stent into a self-expanding stent delivery system according to claim 3, wherein the separate and distinct lubricating material comprises glycerol.

7. The system for loading a self-expanding stent into a self-expanding stent delivery system according to claim 3, wherein the film wrap member comprises a polytetrafluoroethylene film.

8. The system for loading a self-expanding stent into a self-expanding stent delivery system according to claim 3, wherein the transfer tube comprises a polytetrafluoroethylene cylinder.

\* \* \* \* \*